(12) United States Patent
Melman et al.

(10) Patent No.: US 10,499,854 B2
(45) Date of Patent: Dec. 10, 2019

(54) ELIMINATING ACQUISITION-RELATED ARTIFACTS IN ELECTROPHYSIOLOGICAL RECORDING

(71) Applicant: Cochlear Limited, Sydney (AU)

(72) Inventors: Ryan Orin Melman, Sydney (AU); Justin James Gilmour, Sydney (AU); Alex von Brasch, Sydney (AU); Todd Lupton, Sydney (AU)

(73) Assignee: Cochlear Limited, Macquarie University, NSW (AU)

( * ) Notice: Subject to any disclaimer, the term of this patent is extended or adjusted under 35 U.S.C. 154(b) by 210 days.

(21) Appl. No.: 15/361,356

(22) Filed: Nov. 25, 2016

(65) Prior Publication Data

US 2018/0146927 A1 May 31, 2018

(51) Int. Cl.
*A61B 5/00* (2006.01)
*A61B 5/04* (2006.01)
*A61N 1/05* (2006.01)
*A61B 5/12* (2006.01)
*A61N 1/36* (2006.01)

(52) U.S. Cl.
CPC .......... *A61B 5/686* (2013.01); *A61B 5/04001* (2013.01); *A61B 5/04012* (2013.01); *A61B 5/7217* (2013.01); *A61N 1/0541* (2013.01); *A61B 5/12* (2013.01); *A61N 1/36* (2013.01); *A61N 1/36036* (2017.08)

(58) Field of Classification Search
CPC .............. A61B 5/7203; A61B 5/04001; A61B 5/04012; A61B 5/0484; A61B 5/686

USPC .......................................................... 600/547
See application file for complete search history.

(56) References Cited

U.S. PATENT DOCUMENTS

| 5,758,651 A | 6/1998 | Nygard | |
|---|---|---|---|
| 6,295,467 B1 * | 9/2001 | Kollmeier | A61B 5/12 600/547 |
| 8,454,529 B2 | 6/2013 | Daly | |
| 8,945,216 B2 | 2/2015 | Parker | |
| 9,148,734 B2 | 9/2015 | Hillbratt | |
| 9,166,546 B2 | 10/2015 | Swanson | |
| 9,283,376 B2 | 3/2016 | Wouters | |
| 2006/0178706 A1 * | 8/2006 | Lisogurski | A61B 5/04028 607/10 |
| 2006/0287609 A1 * | 12/2006 | Litvak | A61B 5/04001 600/554 |

(Continued)

OTHER PUBLICATIONS

Sampath, et al., "Brainstem auditory evoked potentials for intraoperative neurophysiological monitoring", Journal of Neuroanaesthesiology and Critical Care, vol. 3, 1-3, 2016 (Replacement copy for version filed Dec. 22, 2016).

(Continued)

*Primary Examiner* — Daniel L Cerioni
(74) *Attorney, Agent, or Firm* — Edell, Shapiro & Finnan, LLC

(57) ABSTRACT

Aspects presented herein are directed to techniques for eliminating acquisition related artifacts in electro-physiological recording. In order to eliminate artifacts in neural response recordings, a pair of recordings is made with, respectively, inverted and non-inverted polarity at one pair of electrodes. An average of the two recordings will eliminate the acquisition artifact without the need for an extra recording, such as a baseline.

21 Claims, 11 Drawing Sheets

(56) References Cited

U.S. PATENT DOCUMENTS

| | | | |
|---|---|---|---|
| 2008/0319508 A1* | 12/2008 | Botros | A61B 5/04001 607/57 |
| 2014/0039576 A1 | 2/2014 | Hillbratt | |
| 2014/0275732 A1 | 9/2014 | Hillbratt | |
| 2015/0018699 A1* | 1/2015 | Zeng | A61B 5/04001 600/509 |
| 2015/0258337 A1 | 9/2015 | Long et al. | |
| 2015/0327808 A1* | 11/2015 | Vice | A61N 1/36014 600/388 |
| 2016/0008598 A1 | 1/2016 | McLaughlin et al. | |
| 2016/0027293 A1* | 1/2016 | Esteller | A61B 5/686 340/517 |

OTHER PUBLICATIONS

Sampath, et al., "Brainstem auditory evoked potentials for intraoperative neurophysiological monitoring", Journal of Neuroanaesthesiology and Critical Care, vol. 3, 1-3, 2016.

* cited by examiner

ELIMINATING ACQUISITION-RELATED ARTIFACTS IN ELECTROPHYSIOLOGICAL RECORDING

TECHNICAL FIELD

The technology generally relates to electrophysiological recording, such as by an implant, and more particularly relates to ways of reducing artifacts arising from signal acquisition.

BACKGROUND

Biophysical implants are becoming more common in medicine. Those implants that couple directly to a recipient's nervous system provide a way to control or influence various neurological functions, as well as offer a way to measure biological responses to the implants. Such devices include brain implants, retinal implants and cochlear implants.

Electrophysiology involves measurements of electrical changes and properties of biological cells and tissues, including neurons where the electrical activity is the action potential. A compound action potential (CAP) is the summed responses of a number of neurons firing together.

A widely used and advanced form of biophysical implant is the auditory prosthesis, in particular the cochlear implant (also commonly referred to as cochlear prostheses, cochlear devices, or cochlear implant devices).

Hearing loss, which can have a number of different causes, is generally of two types, conductive (when the normal mechanical pathways of the outer and/or middle ear are impeded), and/or sensorineural (when there is damage to the inner ear, or to the nerve pathways from the inner ear to the brain).

Those suffering from some forms of sensorineural hearing loss benefit from implantable auditory prostheses that electrically stimulate nerve cells of the recipient's auditory system. Cochlear implants are typically prescribed when the sensorineural hearing loss is due to the absence or destruction of the cochlea hair cells, whose prime role is to transduce acoustic signals into nerve impulses.

Cochlear implants generally include a stimulating assembly implanted in a recipient's cochlea to deliver electrical stimulation signals to the auditory nerve cells, thereby bypassing absent or defective hair cells in the cochlea. The electrodes of the stimulating assembly differentially activate auditory neurons that normally encode differential pitches of sound. This assembly enables the brain to perceive a hearing sensation resembling the natural hearing sensation normally delivered to the auditory nerve from the hair cells. An exemplary cochlear implant system is sold by Cochlear Limited (Sydney, Australia) under the Nucleus® brand.

Cochlear implants have historically comprised a receiver/stimulator unit implanted in the recipient's mastoid bone, and an external speech processor unit worn on the body of the recipient which wirelessly transmits information to the implant via RF signals or some other suitable wireless data and/or audio transmission scheme. More recent trends include combining the external and implanted units to produce a "totally implantable cochlear implant" (TICI) capable of operating, at least for a period of time, without the need for an external device.

In any case, the speech processor detects external sound and converts that sound into a coded signal via a suitable speech processing algorithm. From an external unit, the coded signal is sent to the implanted receiver/stimulator unit via a transcutaneous link. For a totally implanted system, detected sound is directly processed by a speech processor within the stimulator unit, with the subsequent stimulation signals delivered without the need for any transcutaneous transmission of signals. Regardless of where the external sound is detected, the receiver/stimulator unit processes the coded signal to generate a series of stimulation sequences which are then applied directly to the auditory nerve via an array of electrodes positioned within and proximal to the modiolus of the recipient's cochlea.

The effectiveness of auditory prostheses depends not only on their specific design but also on how well a prosthesis is configured for, or "fitted" to, the recipient. The fitting, sometimes referred to as "programming" or "mapping" of the prosthesis, creates configuration settings and other data (commonly referred to as a MAP) that define the specific characteristics of the signals (acoustic, mechanical, or electrical) delivered to the recipient. This requires obtaining data about the actual performance of the electrode array following implantation, as well as the response of the auditory nerve to stimulation. Such data collection enables detection and confirmation of the normal operation of the device, and allows the stimulation parameters to be optimized (fitted) to suit the needs of the recipient.

Typically, fitting is manually performed by applying stimulation pulses for each channel and receiving an indication from the implant recipient as to the level and comfort of the resulting sound that the recipient perceives. (As used herein, a channel is the collection of two or more electrodes between which current may be caused to flow to create an auditory percept.) For implants with a large number of channels for stimulation, this process is quite time consuming and rather subjective as it relies heavily on the recipient's subjective impression of the stimulation rather than an objective factor such as a specific measurement. This aspect is further complicated in the case of children and pre-lingual or congenitally deaf patients who are unable to supply an accurate impression of the resulting hearing sensation when asked. In such cases, an incorrectly fitted implant may result in the recipient not receiving optimum benefit from it, and in the case of children, may directly hamper their speech and hearing development. Therefore, there is a need to obtain accurate objective measurements of patient specific data especially in cases where reliable subjective feedback is not possible.

One method of interrogating the performance of the implanted device is to directly measure electrically evoked compound action potentials (EECAPs). The term "evoked" is used herein in a manner synonymous with stimulation: a new response (super-imposed on the basal response of the nerve) is created as a result of an input stimulus. Following electrical stimulation, the neural response is caused by the superposition of single neural responses at the outside of the axon membranes. The EECAP can then be measured as the collective response of all neurons within a nerve or nerve portion to various stimulations, and from this the performance of the implant can be assessed and patient parameters can be interpolated. Neural response telemetry (NRT) is another term used in the art for measures of the responses of nerve cells to an evoked electrical potential. Thus, recording an EECAP with a cochlear implant provides an objective measurement of the response of the auditory nerve to an electrical stimulus (as delivered by an implant electrode).

Additionally, the measurement of ECAPs has provided a useful objective quantification of many applications, such as cortical recordings, auditory brain stem recordings, and electrocochleography ("ECOG"). The last of these, ECOG, measures auditory nerve responses that are evoked acoustically rather than electrically, which means that the measured response includes contributions from the motions of the hairs in the inner ear, the distension of the basal membrane, as well as other physiological effects.

A number of methods and devices to measure evoked compound action potentials (ECAPs) have been developed for cochlear implants. Such systems have used the electrodes implanted within the cochlea to both deliver electrical stimulation and to detect the responses of the nerves to such stimulation.

An aural ECAP comprises contributions from several points along the auditory pathway between the outer ear and the inner brain. The contributions are generally referred to via the wave number. Waves I and II are understood to arise primarily from the cochlea nucleus; waves III-V are typically thought to arise from the brain stem responses; and waves VI and VII are typically thought to correspond to mid brain responses. Cortical responses arise from higher level processes and have much higher latencies still.

Nevertheless, systems for measuring ECAPs still have a number of intrinsic limitations, which have affected the quality of measurements of the neural responses made with them. In the main, this has been due to the presence of artifacts in the measured responses, which mean that the measurement is not necessarily a true indication of the actual ECAP response.

The process of distinguishing the actual ECAP from artifacts has presented considerable difficulties, such as the fact that the signals to be measured are extremely small (down to around 10 µV) in comparison to the size of the stimulus itself, which is typically many orders of magnitude greater (having an amplitude in the range of 1 V to 10 V).

Providing a system that is able to both deliver a stimulus of sufficient amplitude and to detect the elicited response of the nerves to that stimulus has therefore been challenging. Furthermore, due to the nature of the neural response, the detection system must be ready to record the response within a short delay (preferably less than 50 µs) after completion of the stimulus. In order to properly resolve the very small neural response signal from that of the stimulus, a large amplifier gain is required (typically of about 60 dB to 70 dB). But since the neural signal of interest is often superimposed on a much larger artifact, it is difficult to extract the neural signal due to the finite dynamic range of the amplifier and the need for high gain to resolve the signal.

In the past, many systems have simply ignored the artifacts due to acquisition and stimulation, and were not overly concerned about noise in the signal. Others have deployed advanced preparation and shielding techniques, but these are time consuming and laborious to apply, particularly in a surgical setting. Another way in which useful measurements have been separated from the associated artifacts has been through the use of extensive post processing techniques, such as filtering (e.g., by mathematical methods such as principal/independent component analysis (PCA, ICA)). These techniques have applied complicated algorithms to the raw measurements in an attempt to cancel out the presence of the artifacts. Such processes do not provide immediate results which can be acted upon during the fitting process, since the measured results often require time consuming analysis before they can be used. In other approaches, electrophysiological measurements require several baseline measurements, made without stimulation, in order to separately record the artifacts introduced by the acquisition system alone. This baseline measurement—where there is no stimulus artifact—is ultimately subtracted from subsequent averaged measurements of a stimulated response in an attempt to remove the acquisition artifacts. Averaging the measurements ensures the recording is not contaminated with neural responses, such as from spontaneous firing in the periphery (other brain activity in cortical and brain stem measurements). Even the act of inserting an electrode array into the cochlear (while simultaneously taking measurements) can lead to pressure of the electrode array against internal structures, which may evoke neural firing.

The need to take a baseline measurement slows the overall electrophysiological acquisition process, and it has been found to introduce additional noise into the measured results. Baseline subtraction methods and filtering are implemented at the signal processing stage, and do not therefore require adjustments to the electronic circuitry but are part of the programming of the system that captures the signal.

In still other approaches, the acquisition system components are modelled, and then the models are subtracted from the measured signals. But such methods depend on establishing reliable models and some level of calibration, neither of which is straightforward.

In yet other approaches, it is possible to differentiate a neural response from stimulus artifacts by one of two primary methods: forward masking, and alternating stimulation polarity. Forward masking has generally been the more effective of the two techniques. Forward masking involves defining two signals: a probe and mask. A probe is the stimulus that evokes a response. A mask is a secondary stimulus applied before the probe in time, which has the effect of putting the nerve into a refractory state so that it does not fire in response to the probe. This therefore "masks" the effect of the probe, thereby suppressing the response in the subject. The combination of the masker and probe stimulus results in a stimulation artifact which has no neural response present. If two measurements are made, one of the probe alone, and one of the probe-mask combination, the latter can be subtracted from the probe only measurement to remove the stimulation artifact (which is present in both measurements), and thereby isolate the neural response. Alternating stimulation polarity is achieved via dedicated switching circuitry in the stimulation system. Both of these techniques, masking and alternating stimulation, can be used in conjunction with the methods of reducing the acquisition-related artifact, as further described herein.

Overall, given the need to measure the response of nerves to electrical stimulation in many applications, not just in the area of cochlear implants, improvements in accuracy would be welcome. A reliable measurement of the ECAP in response to a given stimulation, would permit the effectiveness of the stimulation to be assessed in relation to the neural response that it evokes. There are various different points of potential measurement along the auditory signal chain. Other waveforms in the chain correspond to higher order functions of the brain, which can be measured in similar ways to ECAPs.

The discussion of the background herein is included to explain the context of the technology. This is not to be taken as an admission that any of the material referred to was published, known, or part of the common general knowledge as at the priority date of any of the claims found appended hereto.

Throughout the description and claims of the application the word "comprise" and variations thereof, such as "comprising" and "comprises", is not intended to exclude other additives, components, integers or steps.

SUMMARY

The technology includes a method of alternating recording electrode polarity in order to eliminate acquisition related artifacts in electrophysiological recording. It has been found that the amplifier in the recording circuitry introduces systematic effects independent of its connections. In order to eliminate artifacts in neural response recordings, two recordings are made with, respectively, inverted and non-inverted polarity at one pair of electrodes. Thus, during the course of measurements, only the inputs to a differential amplifier are changed. One component of the recording artifact is introduced by the electronics of the acquisition system itself. This is mainly the switch on or acquisitional artifact. Rather than eliminate this by subtracting the result of a recording without stimulus from the actual recording, two recordings based on an alternation of the polarities of the active and reference electrode are used. This alternates the polarity of the external signal but not the internal electrical artifact. Hence the average of the two recordings will eliminate the acquisition artifact without the need for an extra recording of, say, a baseline.

Benefits and advantages of the technology include: first, a reduction of the noise floor in electrophysiological measurements by a factor of up to $\sqrt{2}$ (assuming that the stimulus recording and baseline recordings are performed with an equal number of respective averages); and second, a reduction in overall measurement time. As a specific example, in NRT, measurement times can be reduced by 25% relative to the standard forward masking paradigm, provided that the recording polarity is inverted for exactly half the measurements. In this case the switch-on measurements are not required by using the method described herein).

DETAILED DESCRIPTION

The methods and devices herein can function with a variety of types of implant though they have particular benefits when applied to auditory prostheses. Although described herein with respect to cochlear implant systems, it would be within the capability of those skilled in the art to adapt the teachings herein to other types of implant.

The instant technology provides a way to reduce the time required to eliminate the acquisition related artifact, without having a negative impact on noise or the other contributions to the signal.

Cochlear Implants

Figure 1:
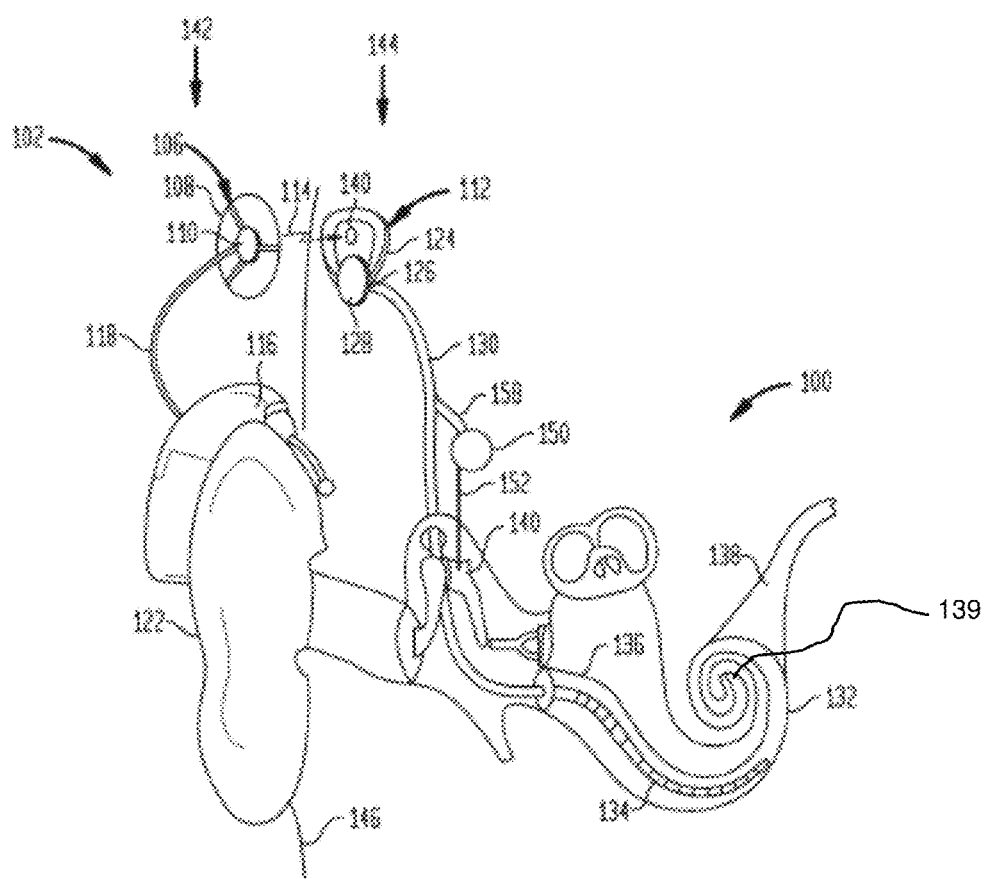
FIG. 1 shows a diagram of a human cochlear, and a suitably positioned cochlear implant.

FIG. 1 is a schematic diagram of an exemplary cochlear implant system 100 which may be fitted to a subject in accordance with embodiments of the present invention. This exemplary cochlear implant system 100 has single- and mixed-mode operational capabilities. With regard to an electrical stimulation mode of operation, cochlear implant system 100 provides direct electrical stimulation of auditory nerve cells to bypass absent or defective hair cells that normally transduce acoustic vibrations into neural activity. In this exemplary cochlear implant, system 100 comprises external component assembly 142 which is directly or indirectly attached to the body of a subject, and an internal component assembly 144 which is temporarily or permanently implanted in the subject. External assembly 142 typically comprises at least one audio pickup device such as a microphone (not shown) for detecting sounds, a speech processing unit 116 that converts the detected sounds into a coded signal, a power source (not shown), and an external transmitter unit 106. External transmitter unit 106 comprises an external transmitter antenna coil 108, and, preferably, a magnet 110 secured directly or indirectly to external coil 108. Speech processor 116 processes the output of the audio pickup devices that may be positioned, for example, by the ear 122 of the subject. Speech processor 116 generates stimulation signals which are provided to external transmitter unit 106 via cable 118.

Internal components 144 comprise an internal receiver unit 112, a stimulator unit 126, and an electrode array 134. Internal receiver unit 112 comprises an internal receiver coil 124 and a magnet 140 fixed relative to coil 124. Internal receiver unit 112 and stimulator unit 126 are hermetically sealed within a housing 128. Internal coil 124 receives power and data from transmitter coil 108. A cable 130 extends from stimulator unit 126 to cochlea 132 and terminates in an electrode array 134. The received signals are applied by array 134 to basilar membrane 136 thereby stimulating auditory nerve 138. Typically, the electrodes differentially activate auditory neurons that normally encode differential pitches of sound.

Collectively, transmitter antenna coil 108 (or more generally, external coil 108) and receiver antenna coil 124 (or, more generally internal coil 124) form an inductively-coupled system of a transcutaneous transfer apparatus 102. Transmitter antenna coil 108 transmits electrical signals to the implantable receiver coil 124 via a radio frequency (RF) link 114. Internal coil 124 is typically a wire antenna coil comprised of at least one and preferably multiple turns of electrically insulated single-strand or multi-strand platinum or gold wire. The electrical insulation of internal coil 124 is provided by a flexible silicone molding (not shown). In use, implantable receiver unit 112 may be positioned, for example, in a recess of the temporal bone adjacent ear 122 of the recipient.

Electromechanical transducer 150 is coupled to the middle ear or inner ear using methods known in the art. Typically, transducer 150 stimulates an impaired inner ear via an air gap coupling. In the embodiment of FIG. 1, electromechanical transducer 150 is coupled to the incus 140 via a coupling rod 152 permanently attached to the outside of membrane 136. Optionally, coupling rod 152 can be attached to the membrane via a coupling element which is connected to the coupling rod.

In an alternative embodiment, transducer 150 can be an electromagnetic transducer arrangement as is described in commonly owned U.S. Pat. No. 6,162,169 which is hereby incorporated by reference herein. In such an embodiment, the transducer arrangement comprises a housing which can be fixed at the implantation site with reference to the skull, with a mechanically stiff coupling element which can move relative to the housing. In the housing there is an electro-mechanical transducer which to vibrates the coupling element.

The signal processing components of the cochlear implant are controlled by a microcontroller located, for example, in speech processor 116. The microcontroller includes a storage area in which subject-specific audiological adaptation parameters and the audiometry parameters of the signal generator are stored. The microcontroller and associated data storage may be implantable, such as within stimulator unit 126. In such embodiments, the programmable data are sent to the microcontroller via telemetry unit 102.

As further described herein, there may be a substantial number of parameters which may be customized to optimally fit a cochlear implant system to an individual subject.

Figure 2:
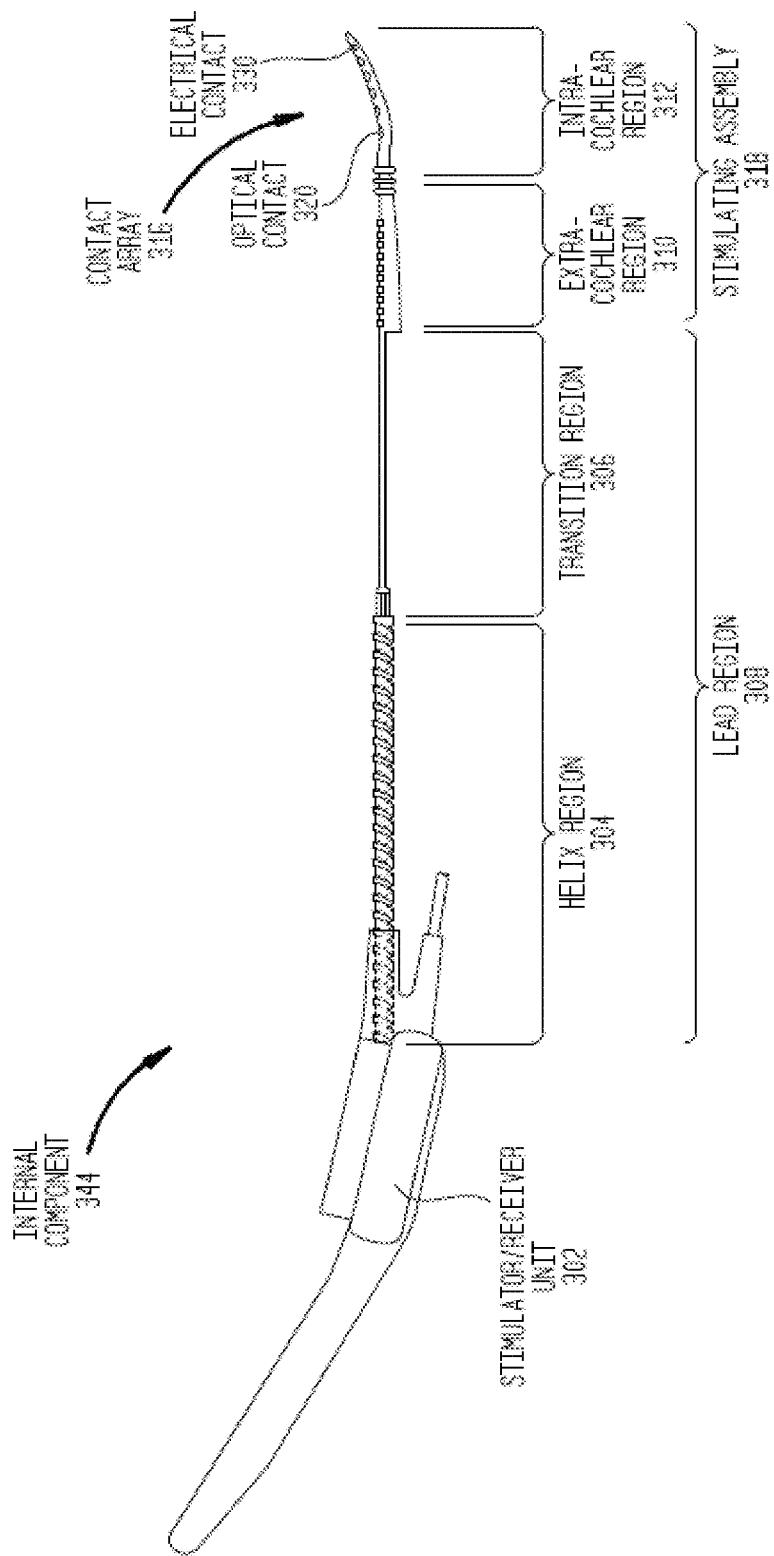
FIG. 2 shows an electrode stimulating assembly of a cochlear implant.

FIG. 2 is a simplified side view of an internal component 344 of a cochlear implant having a stimulator/receiver unit 302 which receives encoded signals from a speech processing unit (not shown). The speech processing unit can be an external or other component of the cochlear implant system. Internal component 344 comprises a lead region 308, connected to the stimulator/receiver unit 302. Lead region 308 further comprises a helix region 304 and a transition region 306. Internal component 344 terminates in a stimulating assembly 318 that is connected to the transition region 306 and comprises an extra-cochlear region 310 and an intra-cochlea region 312. Intra-cochlea region 312 is configured to be implanted in the recipient's cochlea and has disposed thereon a contact array 316. In the example shown, contact array 316 comprises both optical contacts 320 and electrical contacts 330. Some embodiments use electrical contacts only, but some embodiments are based on optical stimulation alone or in conjunction with electrical or other stimulation mechanisms. There are a variety of types of intra-cochlea stimulating assemblies 318 including non-peri-modiolar (such as short, straight), and peri-modiolar.

A peri-modiolar stimulating assembly is configured to adopt a curved configuration during and/or after implantation into the recipient's cochlea. To achieve this, in certain arrangements, stimulating assembly 318 is pre-curved to the same general curvature of a cochlea. Such forms of stimulating assembly 318, are typically held straight by, for example, a stiffening stylet (not shown) or sheath which is removed during implantation, or alternatively varying material combinations or the use of shape memory materials, so that the stimulating assembly may adopt its curved configuration when in the cochlea. Other methods of implantation, as well as other types of stimulating assemblies which adopt a curved configuration, may be used.

Stimulating assembly 318 can also be a non-perimodiolar stimulating assembly. For example, stimulating assembly 318 may comprise a straight stimulating assembly or a mid-scala (not shown in the figure) assembly which assumes a mid-scala position during or following implantation.

Alternatively, the stimulating assembly may be a short electrode implanted into at least the basal region 136 of the cochlea. The stimulating assembly may extend towards the apical end of the cochlea, referred to as the cochlea apex 139. In certain circumstances, the stimulating assembly may be inserted into the cochlea via a cochleostomy.

Internal component 344 further comprises a lead region 308 coupling stimulator/receiver unit 302 to stimulating assembly 318. Lead region 308 comprises a region 304 which is commonly referred to as a helix region. Nevertheless, the required property is that the lead region accommodate movement and is flexible, and it does not need to be formed from wire wound helically. The lead region also comprises a transition region 306 which connects helix region 304 to stimulating assembly 318. As further described below, optical and/or electrical stimulation signals generated by stimulator/receiver unit 302 are delivered to contact array 316 via lead region 308. Helix region 304 prevents lead region 308 and its connection to stimulator/receiver 302 and stimulating assembly 318 from being damaged due to movement of internal component 344 (or a part of it), which may occur, for example, during mastication.

Figure 3:
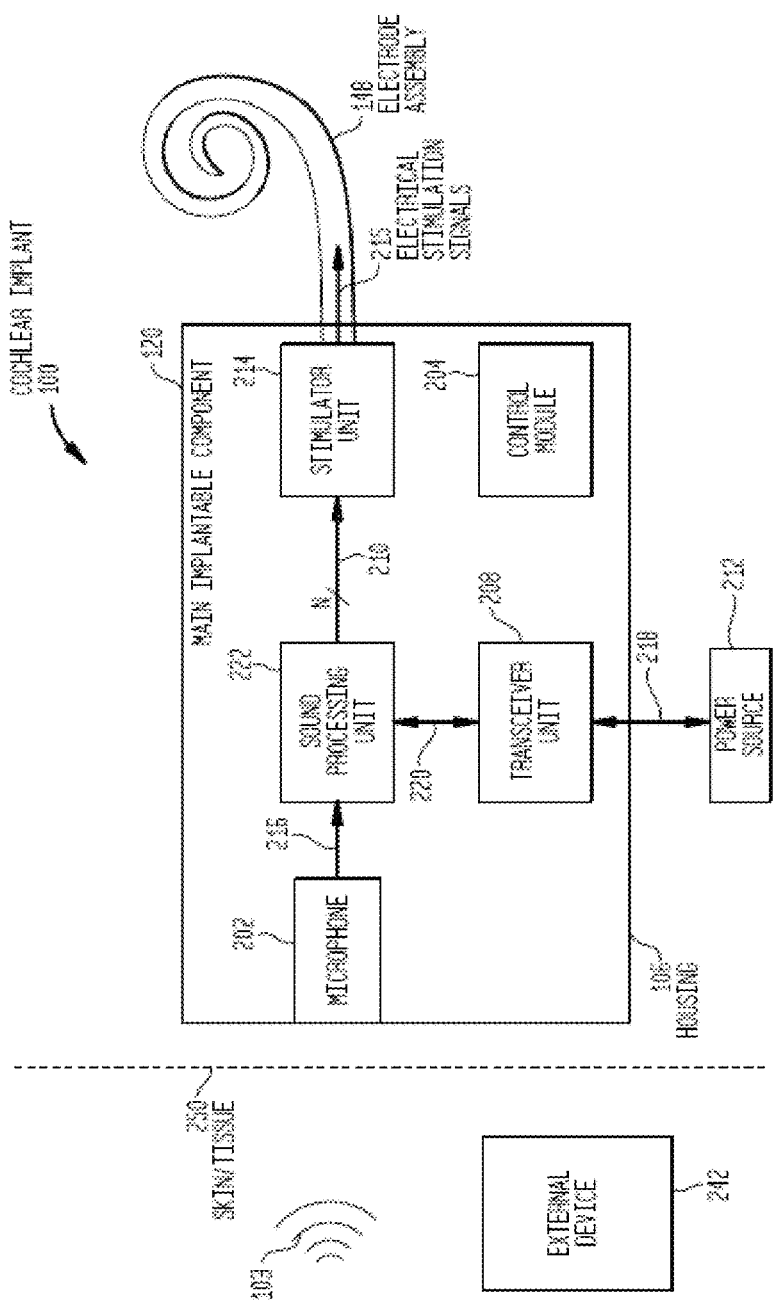
FIG. 3 shows a schematic of the components of a totally implantable cochlear implant.

FIG. 3 is a functional block diagram of the arrangement of the elements of an exemplary totally implantable cochlear implant system 100. In a totally implantable embodiment, all components of cochlear implant system 100 are configured to be implanted under the skin or in the tissue 250 of a recipient. When all components of cochlear implant system 100 are implantable, cochlear implant system 100 operates, for at least a finite period of time, without the need of an external device. Optionally, an external device 242 can be used to charge the internal battery, to supplement the performance of the implanted microphone/system, or for when the internal battery no longer functions. External device 242 may be a dedicated charger or a cochlear implant sound processor.

As noted, cochlear implant system 100 in FIG. 3 includes a main implantable component 120 having a hermetically sealed, biocompatible housing 106. Disposed in main implantable component 120 is a microphone 202 configured to sense a sound 103. Microphone 202 may include one or more components to pre-process the microphone output. As an alternative embodiment, as shown in FIG. 3, the cochlear implant is a totally implantable system, and the microphone does not need to be integrated into a unitary implant body. The microphone and other aspects of the system can be included in a tethered module (connected via a lead wire like the electrode array) or a specially designed plug for external component attachment.

An electrical signal 216 representing sound signal 103 detected by microphone 202 is provided from the microphone to sound processing unit 222. Sound processing unit 222 implements one or more speech processing and/or coding strategies to convert the pre-processed microphone output into data signals 210 for use by stimulator unit 214. Stimulator unit 214 utilizes data signals 210 to generate electrical stimulation signals 215 for delivery to the cochlea of the recipient.

In the example of FIG. 3, cochlear implant system 100 comprises electrode assembly 148 for delivering stimulation signal 215 to the recipient's cochlea.

Cochlear implant system 100 also includes a rechargeable power source 212. Power source 212 may comprise, for example, one or more rechargeable batteries. As described below, power can be received from an external device 242, and is stored in power source 212. The power may then be distributed to the other components of cochlear implant system 100 as needed for operation.

Main implantable component 120 further comprises a control module 204 that includes various components for controlling the operation of cochlear implant 100, or for controlling specific components of cochlear implant system 100. For example, controller 204 may control the delivery of power from power source 212 to other components of cochlear implant system 100. For ease of illustration, main implantable component 120 and power source 212 are shown separate from one another. However, power source 212 can alternatively be integrated into a hermetically sealed housing 106 or be a part of a separate module coupled to component 120.

As noted above, cochlear implant system 100 further comprises a receiver or transceiver unit 208 that permits cochlear implant system 100 to receive and/or transmit signals to an external device. For ease of illustration, cochlear implant system 100 is shown having a transceiver unit 208 in main implantable component 120. In alternative arrangements, cochlear implant system 100 includes a receiver or transceiver unit which is implanted elsewhere in the recipient outside of main implantable component 120.

Transceiver unit 208 can be configured to transcutaneously receive power and/or data from external device 242. As used herein, transceiver unit 208 refers to any collection of one or more implanted components which form part of a transcutaneous energy transfer system. Furthermore, transceiver unit 208 includes any number of component(s) which receive and/or transmit data or power, such as, for example a coil for a magnetic inductive arrangement, an antenna for an alternative RF system, capacitive plates, or any other suitable arrangement. Various types of energy transfer, such as infrared (IR), electromagnetic, capacitive and inductive transfer, can be used to transfer the power and/or data from external device 242 to cochlear implant system 100.

In some embodiments, transceiver unit 208 can receive power and/or data from external device 242. In one such arrangement, external device 242 comprises a power source (not shown in FIG. 3) disposed in a behind-the-ear (BTE) unit. External device 242 also includes components of a transcutaneous energy transfer link formed with transceiver unit 208 to transfer the power and/or data to cochlear implant system 100. The external device shown in FIG. 3 is merely illustrative, and other external devices having different functions can be alternatively used.

Although ideally suited to a cochlear implant, the methods described herein can be applied to other implants. In particular, the methods are suited to implantable devices that utilize a differential amplifier to record a potential in the body as a response to a stimulus. In auditory applications, such implants can be those used in ECOG generally. In a preferred embodiment, the amplifier is a differential amplifier (which amplifies the difference between two inputs). In order to minimize the number of measurements that are taken, only the inputs to the differential amplifier are changed.

Electrophysiological Recording

Figure 4A:
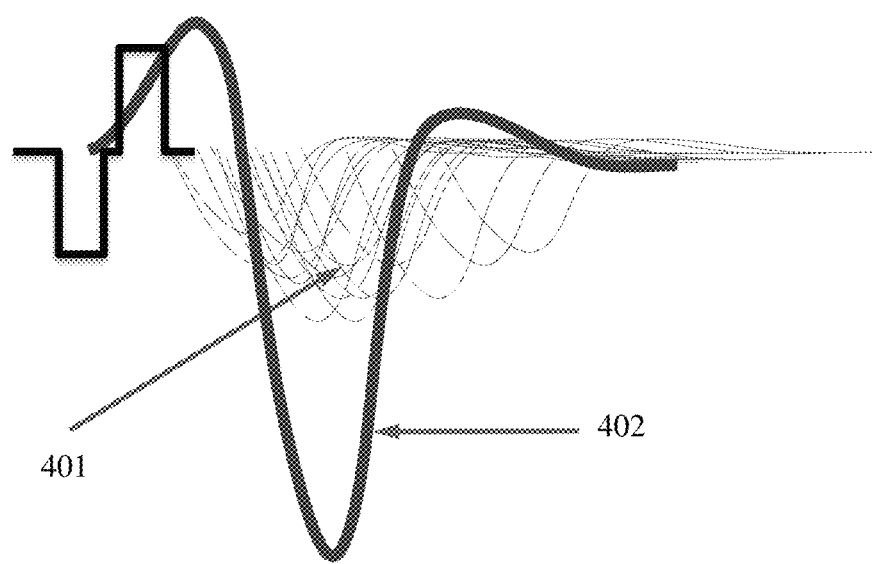
FIG. 4A shows a schematic of neural contributions to an electrically evoked compound action potential.
Figure 4B:
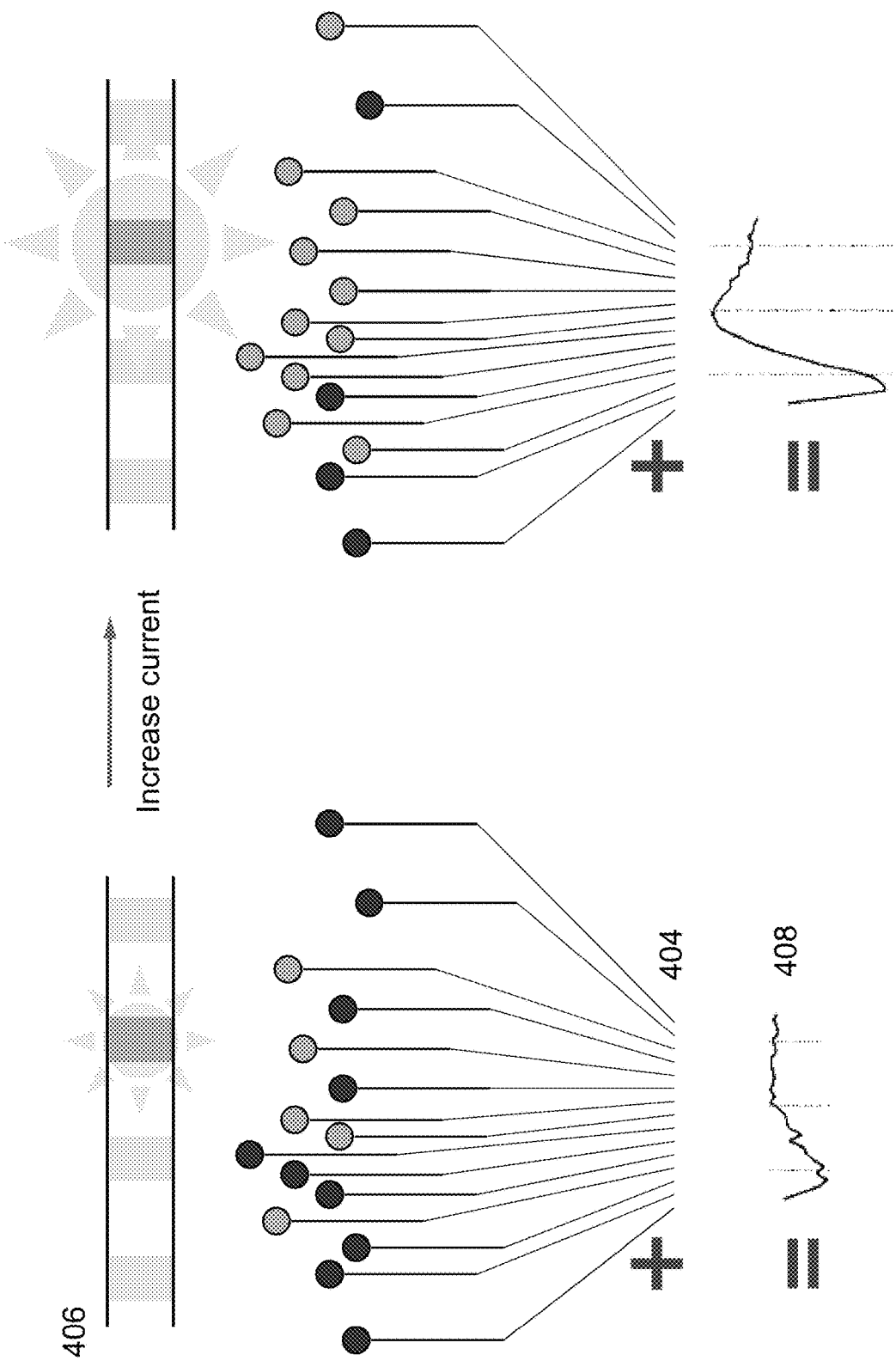
FIG. 4B shows how multiple neurons can be stimulated by a pulse to a single electrode.

In summary, the steps to obtain an electrophysiological recording from a cochlear implant, such as via neural response telemetry (NRT), are that an audiologist selects one of the electrodes, in electrical contact 330, FIG. 2, inside the cochlea to stimulate. A brief set of current pulses is delivered to that electrode. These excite auditory nerve fibers located close to the stimulating electrode and cause them to fire. Another electrode inside the cochlea is selected to record the electrical activity from the nerves, and the results are amplified, digitized and then transmitted across the skin barrier to an externally worn coil (108 in FIG. 1). This coil sends information through the sound processor back to a computer where the result is seen as a trace on the screen. The audiologist can recognize if the trace is from a neural response from the shape of the waveform. (For example, a neural response signal gets larger with current level, and disappears completely when below the noise floor.) Recognizing the waveform can also be done automatically via an expert system that correlates the latency and amplitude of the measurement with a typical expected form(s) of response. The form of the signal is complicated by the fact that a given neuron can only fire at certain rates, and has three distinct states: fired, resting and baseline. If a neuron is excited with an electrical pulse, it will fire, but, because it is then saturated and requires a certain time to relax to its resting state, typically approximately 1 ms., it won't fire again for at least that period of time (known as the absolute refractory period). From the resting state, the nerve can fire again, but it requires more current then from its baseline state until it has fully relaxed back to its baseline state. This period is known as the relative refractory period. The recorded signals from the nerves are very small—in the nV to mV range. In general it is only possible to measure the signals because a lot of neurons are stimulated together. This is shown schematically in FIGS. 4A and 4B. In FIG. 4A, individual neuron action potentials (APs) 401, stochastically distributed, are summed to form compound AP 402. In FIG. 4B, the auditory nerve 404 is shown schematically as a bundle of neurons. An array of electrodes 406 is situated so that stimulating current can be delivered to the nerve. Increasing current to an electrode proximate to the nerve increases the number of neurons that are stimulated, and causes a corresponding increase in the action potential 408.

Figure 5A:
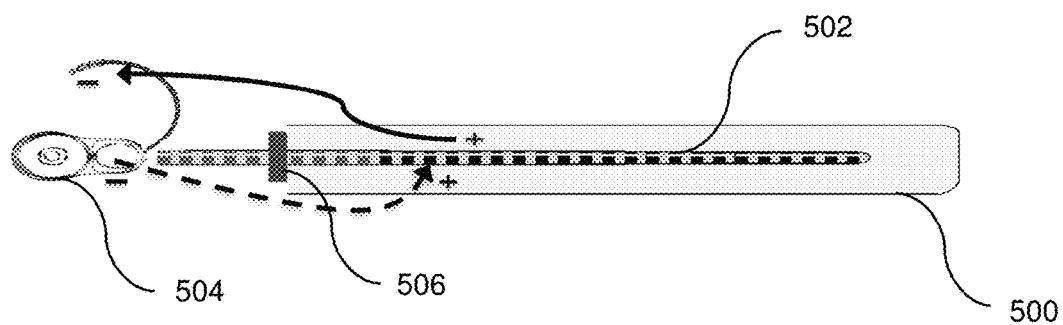
FIG. 5A shows a schematic of standard acquisition polarity for a probe recording (denoted A herein).
Figure 5B:
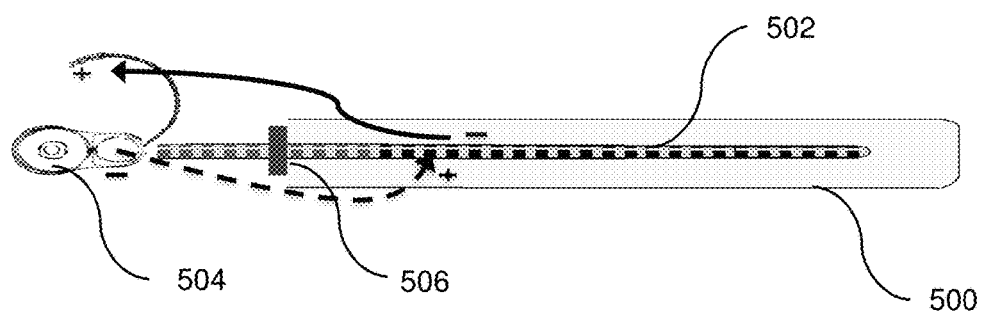
FIG. 5B shows a schematic of inverted acquisition polarity for a probe recording (denoted A' herein).

FIGS. 5A and 5B show a schematic of an electrical contact of a cochlear implant. Electrode array 502 is positioned within cochlea 500, via the cochlea entrance 506, and is coupled to the implanted stimulator packaging 504. The electrode array may have stiffening rings along the portion where it enters the cochlea. Electrode array 502 comprises a number of pairs of electrodes, in electrical communication with the stimulator. Each pair of electrodes comprises an active electrode, which provides the current, and a reference electrode, which acts as a current sink. The electrodes are configured so that they can transmit a voltage to the cochlea to stimulate a nerve, as well as communicate a signal back to the stimulator for recording. In general, the electrical circuitry is configured to stimulate via one pair of electrodes and to record a response on a second, different, pair. Recording on a different pair of electrodes from the stimulating pair usually avoids or minimizes the effect of saturation that results from the stimulation artifact, as further described hereinbelow.

During a typical electrophysiological measurement, FIG. 5A, an electrical stimulus, designated by the arrow having a dashed line in the figure, is sent to a specific electrode pair that applies the stimulus to a neural body such as an auditory nerve, to evoke a compound neural response. The stimulus is delivered over a window of time, referred to as an epoch. A "probe epoch" is one associated with a stimulus intended to evoke a neural response, in which case it is possible to start the recording before the stimulus, or an arbitrary period after it is complete (e.g., wait 100 µs). A probe stimulus doesn't have to arise from a single pulse: the probe can comprise a complex stimulus, such as from a pulse train (a series of pulses at a certain rate), or it can be multipolar, such as delivered from multiple electrodes. It is preferable to have at least 1 epoch per stimulation. In ECOG, say, it can be preferable to have more than one recording window after one stimulus because there are different types of responses at different times after the stimulus.

The response recorded by the sense electrodes (a different pair from those that delivered the stimulus) is designated by the solid line in FIG. 5A. The "+" and "−" signs in the figure show the polarity at the electrode and stimulator respectively in each case.

It is seen that in FIG. 5A, the signal polarity is the same in both stimulation and in recording.

The recorded response is composed of several contributions, including: stimulus artifact; acquisition/measurement/amplifier artifact; target signal (typically a compound neural response); and noise. The acquisition artifact is independent of any signal from the tissue but originates in the recording circuitry alone.

During acquisition (recording) of the response, one of the goals is to maximize the magnitude of the target signal while minimizing the recorded artifacts and noise. The stimulation artifact reduces at a more than exponential rate, starting from the stimulation voltage, which is typically >1,000× larger than the neural response. The artifact is always smaller at later time points in the recording window than at the start of the recording window. The principle of maximizing the target signal while minimizing the artifacts and noise must be balanced with the duration of the recording, to ensure that the recording time does not become untenably long just for the purpose of minimizing the artifacts. (It is preferable to not unduly lengthen the entire process, for the sake of patient comfort, as well as a need to conserve power drawn by the implant on its internal supply.)

The timing of the beginning and the ending of the recording is also important. For example, in one embodiment, the implant amplifier automatically resets itself to zero on the first measurement, so that if the recording is started too soon the signal would sweep through the entire amplifier dynamic range in one or two samples and it would not be possible to extract the response from it. On the other hand, the neural response latency is fixed with respect to the stimulus, meaning that if recording is started too late it is possible to miss capturing the neural response.

Acquisition Artifact

Acquisition artifacts are inherent to the measurement system, and are typically due to internal electrical properties of the cochlear implant. These artifacts are independent of the way in which the implant is connected to the outside world, such as the polarity of the recording electrodes. The acquisition artifact is present as a systematic additive effect and can be eliminated by the subtraction of any second recording made with the system. Hence, baseline subtraction can be used to eliminate acquisition artifacts. Because acquisition artifacts are independent of any signal used to stimulate the implant, the same acquisition artifact is present in the probe recording as a baseline recording or even an inverted probe recording. Thus, when the polarities of the recording electrodes are inverted, the acquisition artifact does not change in magnitude or sign.

Accordingly, a method of eliminating, or substantially reducing, the acquisition artifact, comprises: recording a number of probe epochs with standard acquisition polarity (A), as shown in FIG. 5A, and an equal number of epochs with inverted (sometimes referred to as "reversed") acquisition polarity (A'), as shown in FIG. 5B; then, after optionally aligning the traces, subtracting A' from A, and dividing the resulting signal by 2.

Terms used herein include: "standard recording switching" in which there is no inversion of polarity, and "alternating recording polarity switching"

The premise of the method herein is that when the polarity of the recording electrodes is inverted, the target signal will invert; the acquisition artifact will not invert; and independent noise sources are irrelevant to the overall signal. The aim can alternatively be understood as amplifying the difference between the two signals, thereby accentuating the contributions external to the amplifier, while flattening or cancelling out other contributions within the measurement system.

Figure 8:
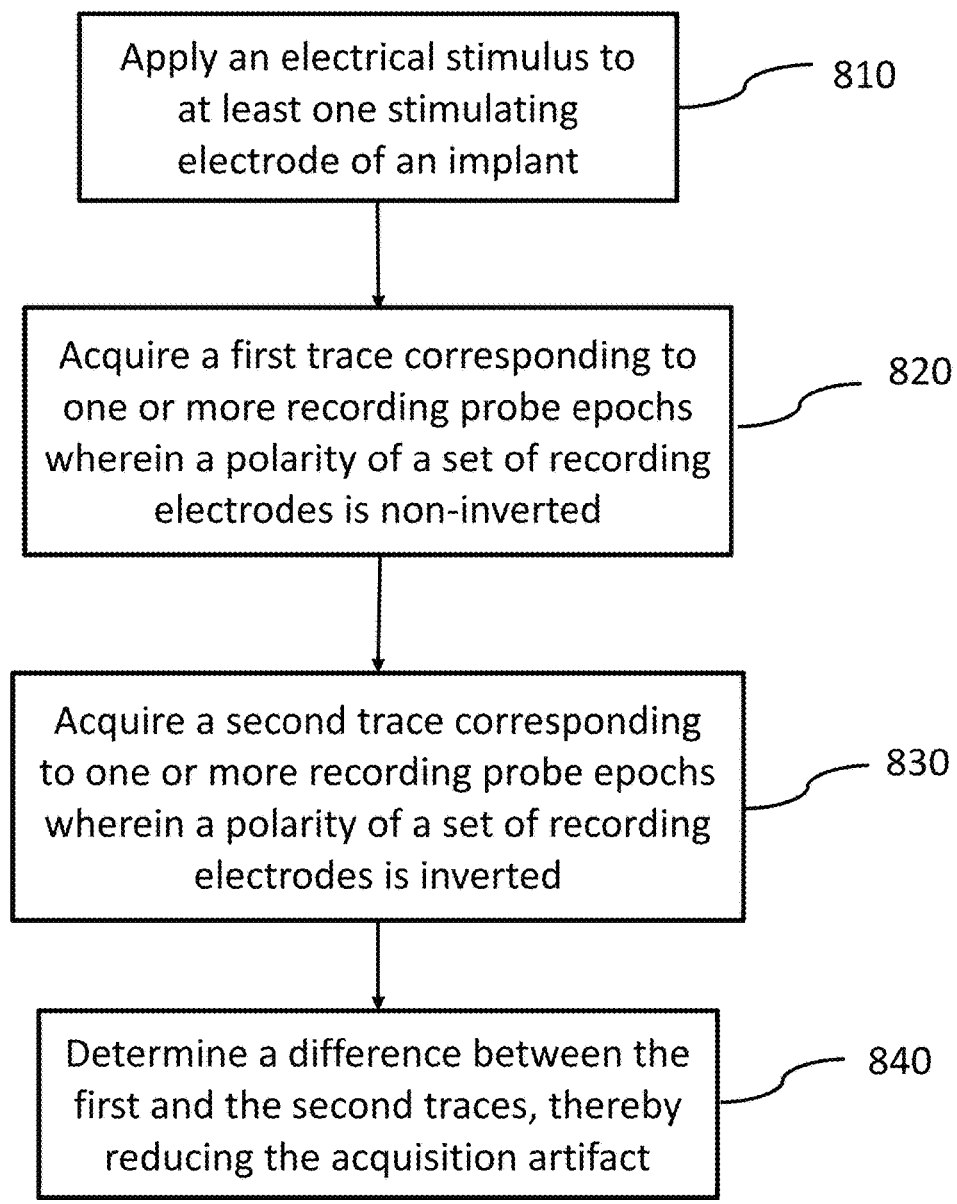
FIG. 8 shows a flow chart of a method herein.

Accordingly, in overview, a method as further described herein is set forth according to the flow-chart in FIG. 8. In order to measure an in vivo electrical potential, an electrical stimulus is applied 810 to at least one stimulating electrode of an implant; then a first trace is acquired 820 that corresponds to one or more recording probe epochs in which a polarity of a set of recording electrodes is non-inverted, and a second trace is acquired 830 that corresponds to one or more recording epochs in which the polarity of a set of recording electrodes is inverted. By determining 840 a difference between the first and the second traces from steps 820 and 830, it is possible to reduce the acquisition artifact.

The recorded epoch signals for each of the acquisitions (A and A') can be described mathematically in Equations (1) and (2), as follows:

$$A = \text{Artifact}_{Stimulus} + \text{Artifact}_{Recording} + \text{Response} + \text{Noise} \quad (1)$$

$$A' = -\text{Artifact}_{Stimulus} + \text{Artifact}_{Recording} - \text{Response} + \text{Noise} \quad (2)$$

Where the term $\text{Artifact}_{Recording}$ is the acquisition artifact. Equation (1) represents the signal recorded with standard acquisition polarity at the recording electrodes, and Equation (2) represents the signal recorded with inverted acquisition polarity.

In one embodiment, several measurements are taken: recording a probe only stimulus (A), and a masker-probe stimulus (B). In practical terms, it does not matter whether trace B is recorded before or after A. A masker stimulus without a following probe (C), is also recorded. By contrast, and by way of illustration, in methods of the prior art, a baseline (i.e., no stimulus) recording (D) is also taken. The D-trace just records the "switch on" of the system, without applying any probe or mask. The D-trace therefore includes only acquisition-related artifacts. Typical processing without using the methods herein, is to manipulate these four recordings, or traces, as follows (Equation (3)), in order to remove one or more artifacts:

$$A - (B - C) - D. \quad (3)$$

The subtraction (B−C) gives rise to just the probe artifact contribution to the signal.

The method herein eliminates the need for measurement D, also referred to as the D-trace, replacing it instead with the A' trace.

Figure 9:
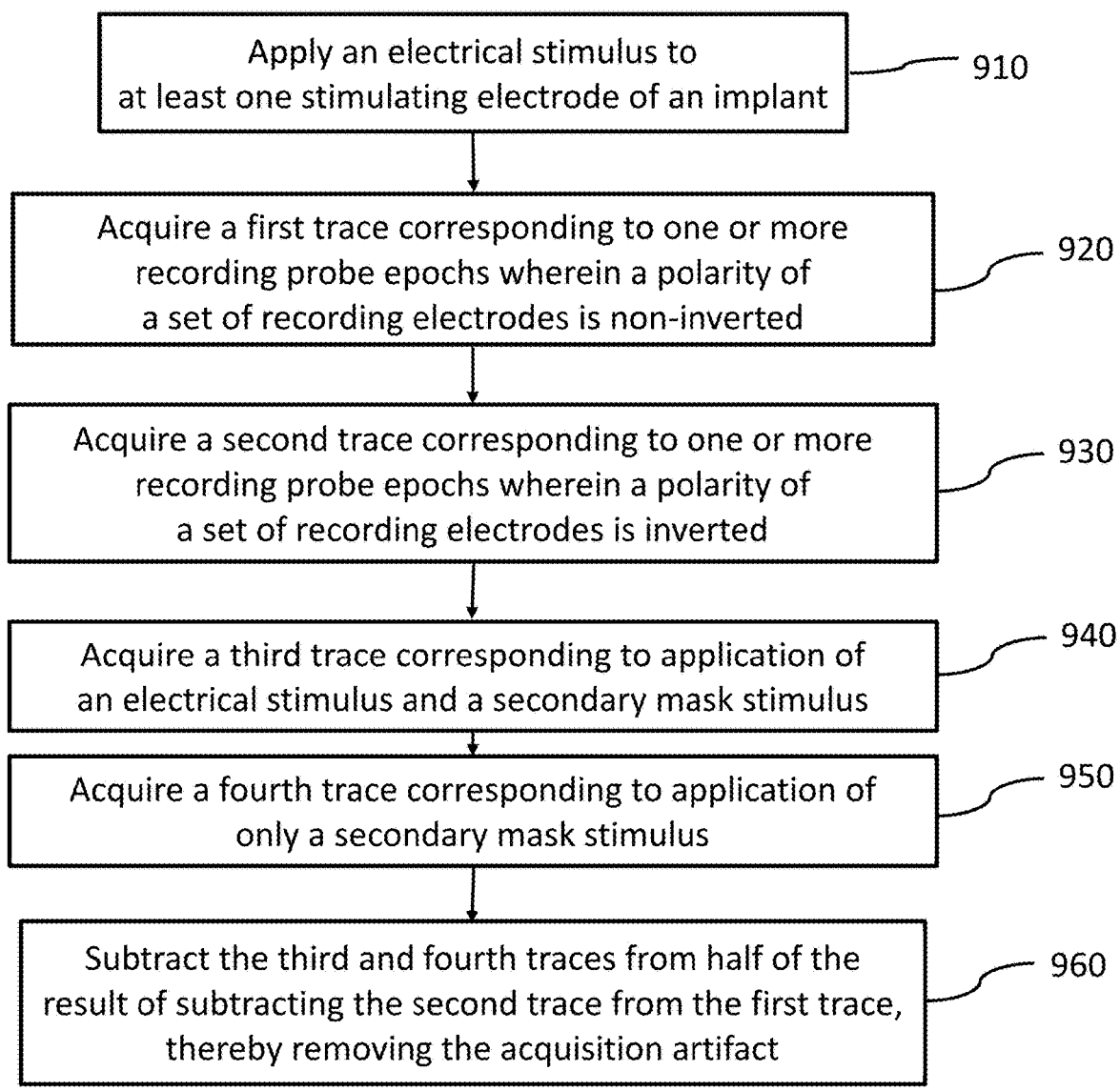
FIG. 9 shows a flow chart of a method herein.

Accordingly, the foregoing method of removing an acquisitional artifact from measurement of an in vivo electrical potential, is set forth in the flow-chart of FIG. 9, wherein: in a first step, applying 910 an electrical stimulus to at least one stimulating electrode of an implant; acquiring 920 a first trace corresponding to one or more recording probe epochs in which a polarity of a set of recording electrodes is non-inverted; acquiring 930 a second trace corresponding to one or more recording probe epochs in which the polarity of a set of recording electrodes is inverted; acquiring 940 a third trace corresponding to application of an electrical stimulus and a secondary mask stimulus; and acquiring 940 a fourth trace corresponding to application of only a secondary mask stimulus. By subtracting 950 the third and fourth traces from half of the result of subtracting the second trace from the first trace, the resulting trace has the acquisition artifact removed.

By using even numbers of averages of both the A and A' traces, the D trace is no longer required as A−A'=2×(Response+Artifact$_{stimulus}$)+residual noise. Note that an equal number of A and A' measurements are required for this simple formulation to work, but this is not to preclude embodiments of the method that rely upon uneven numbers of measurements, which then are processed via weighted averaging.

When measuring A and A', it is preferable to wait long enough for the neurons to return to baseline state between the two measurements, though it is sufficient for them to return to any known state, as stimulus from within the refractory (recovery) period is a well-established technique.

Thus, according to the methods herein, the following traces can be measured, in any order. One trace (a signal measured at a sequence of times) is measured for a probe only (A) in an attempt to measure the neural response. Typically this measurement gives rise to the sum of neural response, stimulation artifact, and acquisition artifact, and a noise contribution. A second stimulus (probe) can be applied but with an inverted polarity (A'). A trace from a masker probe (B) is recorded. A "switch-on" measurement, i.e., masker without probe, trace (C) is also recorded.

The traces then are manipulated, as follows. Traces A and A' are averaged by subtracting A' from A, and halving the result, giving (A−A')/2. This is effectively an "average" because A' is "−A", due to the inverted polarity. Trace (B) is subtracted from (A−A')/2 to remove the stimulation artifact. The recording artifact can be removed by subtracting the "switch-on" measurement, i.e., masker without probe, trace (C). This can be represented by the following equations (4a, 4b):

$$A-(B-C) \quad (4a)$$

$$-A'-(B-C) \quad (4b)$$

When averaging the signals, it is possible to average the calculated waveforms for each epoch or separately average each of the A, B, C and A' measurements and calculate the subtractions in (4a) and (4b) at the end. Either way, the need for trace (D) becomes superfluous.

In another embodiment, A and A' are both measured along with traces B and C, see Equation (4c):

$$(A-A')/2-(B-C) \quad (4c)$$

As an example of the saving in the number of traces that are required, consider obtaining 40 averaged neural response measurements. With the standard forward masking of the art, this requires 40 measurements of each of A, B, C, and D traces, i.e., 160 Epochs. While the foregoing numbers are typical, the technology herein is not so limited to specific numbers.

Based on obtaining 40 averaged neural response measurements, utilizing equations (4a,4b) herein involves measuring 20 A, B, and C traces, along with 20 A', B, and C traces, i.e., only 120 epochs.

Utilizing the protocol in (4c) requires measuring 20 A, A', B, and C traces, i.e., 80-epochs.

Note that the formulation in (4c) will have a different noise profile as the B and C traces are only averaged half the number of times they are in the other measurement paradigms. Depending on whether the noise contributions in the B and C traces are largely quantisation related, correlated or uncorrelated, will determine the desirability of using equation (4c) over that of equations (4a, 4b).

In many cochlear implant systems, the electrode circuitry includes amplifiers that are differential amplifiers, i.e., they amplify the difference in voltage between the two recording electrodes. This means that when the polarities of the recording electrodes are inverted, the recorded signal (comprising stimulus artifact and target signal) also inverts, but the contribution to the signal from the acquisition artifact remains constant. (The difference in voltage is independent of polarity.) When signals are averaged, as described hereinbelow, the signal to noise ratio is improved. By contrast, if independent epochs are summed, they cannot be averaged because they contain signals with independent information.

Signals A and A' are not independent. They contain identical information once we take the difference of A and A', thus the target signal ends up 2× as large as it is in reality and needs to be divided by 2 to restore its original amplitude.

The averaging of the two measurements, leading to elimination of the acquisition artifact, is expressed in Equation (5) as:

$$\frac{A-A'}{2} = Artifact_{Stimulus} + \text{Response} + \alpha \text{Noise} \quad (5)$$

The subtraction of A and A', and division by 2, is equivalent to averaging the target signal (Response). Since the acquisition artifact does not invert when the recording electrodes are inverted whereas the stimulus artifact and response (the other two non-noise contributions to the signal) do, it is eliminated in this process. The stimulus artifact, which remains in the resulting signal, can be removed by other methods known in the art such as a probe-mask set-up or by fitting a model. Because the acquisition artifact is removed in this way, a baseline measurement (a recording taken with no stimulus, subtracted later with the intent to capture the acquisition artifact) is no longer required.

Additionally, not only does the subtraction of A' from A eliminate the acquisition artifact, but the RMS noise is reduced by up to a factor of √2.

In equation (5), α is a coefficient in the range $1/\sqrt{2} < \alpha < 1.0$ that expresses the level of noise reduction. In general, the term "noise" in the equations represents any uncorrelated signal: i.e., any part of the measurement that does not correlate with stimulus or recording. The effect of any uncorrelated contributions to the signals is reduced or eliminated by this method. The noise is independent in all the measurements so it is averaged and thus decreases as specified in Equation (5). Alternatively put, inverting the measurements has no effect on the noise variance. The calculation in equation (5) reduces the noise variance because of the division by 2; by contrast, straight subtraction of two or more traces (as was carried out previously in the art when a baseline signal was measured) increases the noise variance.

Furthermore, as signal averaging is already required during many electrophysiological measurements, the methods herein do not lead to an increase in the total recording time. The same stimulus can be applied for each recording, and the same number of measurements with standard polarity, as measurements with inverted polarity are taken.

The implementation in which two epochs are recorded, and one is subtracted from the other, is not the only way to remove the acquisition artifact, and other computational approaches are possible. In general, the result can be achieved by obtaining a normalized value. For example, measurements can be made in pairs and then averaged, but it is also possible to measure a number of epochs, say 5, 10, 20, or another convenient number, at one polarity then average those measurements, followed by measuring and averaging the same number at another polarity, followed by determining the difference between the two averaged numbers in order to remove the contributions of the acquisition artifact to all the epochs.

The formulae herein apply to measurements from a single pair of electrodes. The methods herein can equally apply to situations in which more than one pair of electrodes makes a recording.

Additionally, the polarity switch described herein can be applied in different ways: either with no averaging and a switch of polarity; or when averaging over a number of measurements, individual measurements can be cancelled out when a recording of the opposite polarity has been made.

There are a number of ways in which the recordings can be carried out and manipulated to give rise to elimination of the acquisition artifact. As described hereinabove, in an approach referred to as "averaging", the following signals are measured: probe (A); masker (B); masker and probe (C), with normal polarity. Then the polarity is switched and the A signal is measured again (giving A'). In some embodiments B and C are also recorded with inverted polarity (giving B' and C'). In this instance, there is no D-trace (baseline) measurement. All the sets of measurements can be repeated and then averaged.

In an alternative embodiment, the A, B, and C traces are each recorded, followed by an A-trace with inverted polarity. No D-trace is recorded. All measurements can also be repeated and averaged. This approach reduces the noise (and removes the acquisition artifact), but does not save on the overall recording time. However, given that it is rare to rely on a single set of measurements (A, A', B and C), when making the recordings over multiple instances, the noise is significantly reduced.

Given that the method reduces the noise as compared to an equivalent method involving a D-trace measurement (with the same number of stimulus epochs), measurements acquired in this manner can be made at lower current levels, which itself may further reduce measurement time for search algorithms that search for the minimum current level at which a neural response can be measured (and for a cochlear implant results in a more comfortable process for the recipient). This is because the neural response amplitude is directly proportional to the current injected. Often, if no ECAP is observed that is because the ECAP amplitude is smaller than the noise floor. One of the measurements typically made when performing a technique such as NRT is to identify the smallest current level which provides an ECAP larger than the noise floor. To do this, starting with a small current level, a number of measurements are performed to identify if an ECAP is present. If it is not, the current level is increased and repeated until the ECAP is detected. Then the current level is decreased again until it falls below the noise floor. Thus, a lower noise floor means that less current is required to produce an observable ECAP, and further means that it is necessary to take fewer measurements to obtain the current level threshold at which the ECAP becomes observable. By lowering the noise floor, it may therefore be possible to identify neural response of smaller amplitude that was previously within or below the previous noise floor. In other words: there is a minimum ratio of (signal amplitude)/(noise floor amplitude) required to be confident that a neural response is being measured. By lowering the noise floor it is possible to inject less current and yet still be able to detect the desired ECAP.

Alternative implementations include off-line analyses, i.e., averaging two recorded signals that have been previously recorded and stored, but it is preferable to apply the subtraction step to remove the artifact at the recording stage so that immediate feedback from the recipient can be properly taken into account.

The method can be implemented in cochlear implant systems, including but not limited to the Nucleus family of devices (from Cochlear Limited, Sydney, Australia).

The method can be deployed in the measurement of other evoked potentials such as the stapedius reflex, EABR (electrical auditory brainstem response), the acoustic reflex threshold, and the cortical evoked response. The method can also be applied to spinal measurements, wherein the improved measurement paradigm may allow for less aggressive filtering.

The method can be further deployed in measurement of in vivo electrical potentials generally, such as within tests that don't necessarily look for an electrophysiological response. Such tests can include in vivo testing for leakage paths where a stimulating current is applied and it is still important to reduce the acquisition artifact. Another example of such a test is a "Current Tracker" in vivo diagnostic test, in which the decay and amplitude of the stimulation artifact following stimulation is observed. (Pollution of the measurement from a neural response or switch on artifact is to be avoided). By contrast, the shape and amplitude of the stimulus artifact, measured after a predetermined hold-off time, provides useful diagnostic information that relates to damage of the silicone carrier surrounding the implant or its electrode array.

Typical approaches in which the method can be deployed include those measurements in which a particular output in response to a stimulus is repeatedly obtained. Recording is repeatable by taking more measurements, to generate a quantity that has the capacity to be averaged. Thus, in the situation where application of a stimulus gives rise to a consistent output in response, then the technique can be used to eliminate the artifact in place of baseline subtraction. On the other hand, if there is a x % probability of response type A, and y % probability of response type B, every time the stimulus is applied, then the technique may not be a very useful. Examples of systems that do not lend themselves well to direct averaging include some cortical measurements or real-time heart rate monitoring.

By using the method described herein, DC drift intra-window can also be minimized. This drift is caused by the implant's voltage rail reducing during the non-power-up period (recording). (When measurements of the implant are made, the implant is running off a capacitor whose voltage is dropping as current is consumed.)

Any electrophysiological acquisition system such as an implant, which has short well-balanced lead wires and a dynamically switched acquisition setup can benefit from this recording methodology. Typically this is any implantable neural stimulator that can acquire physiological signals and is such that there is not a significant systematic difference that results from inverting the recording electrodes.

A benefit of the method is to make the fitting process feasible in the operating room, during a surgical procedure in which a device is implanted into a recipient. With the method herein, it is possible to carry out the fitting process much faster than was previously possible, e.g., in 5 mins. vs. 15 mins.

Figure 7A:
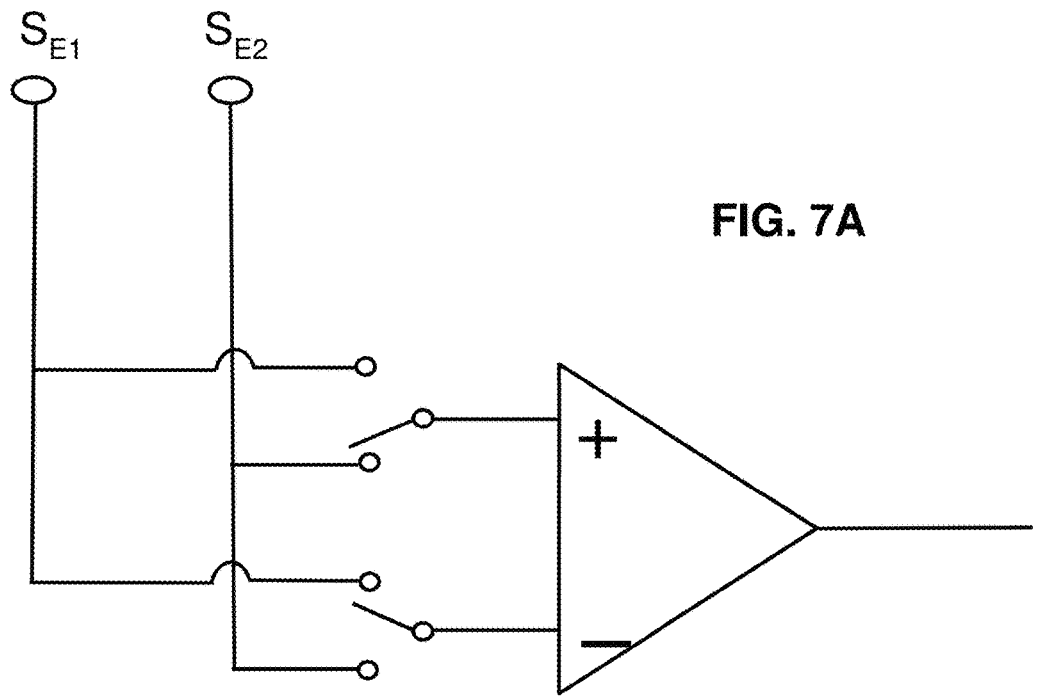
FIGS. 7A and 7B show electrical circuit connections for alternating recordings.
Figure 7B:
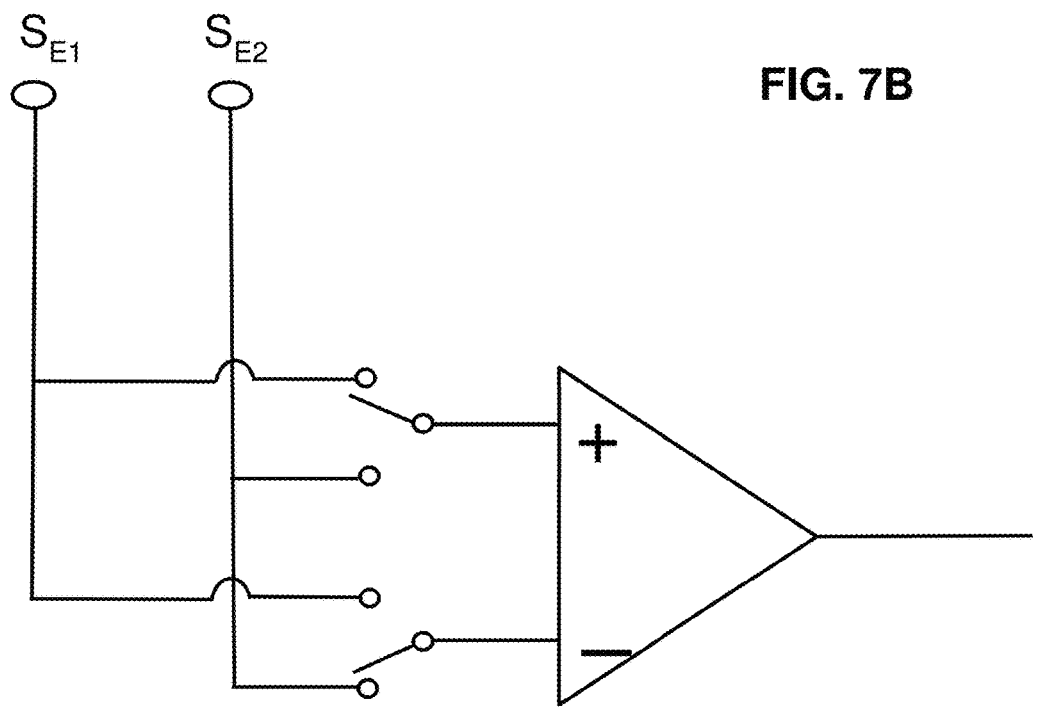

FIGS. 7A and 7B show a portion of a circuit diagram for implementing the method for removing acquisition artifacts. Thus, in FIGS. 7A and 7B, just the differential amplifier part of the acquisition system and a pair of connections to it, are shown. In practice, the circuit portion of FIGS. 7A and 7B will be a part of a switch matrix in which there are switches configured to control which of a number of external electrodes is connected to a single amplifier. In that way, switches control which channel is amplified at a given time. When used with an auditory prosthesis such as a cochlear implant herein, the chosen electrodes are situated inside the cochlea.

Whereas circuitry for measuring and correcting for stimulation artifacts may already have polarity switching circuits built in, such features are not typically found for the recording circuitry. A circuit such as shown in FIGS. 7A and 7B can therefore be retrofit to an existing system for performing, e.g., ECOG. Such a modification therefore incorporates switches on inputs to a differential amplifier where the circuitry to implement other methods such as baseline subtraction does not have switches. Nevertheless, manufacturing switches and implementing them in circuitry is not a significant overhead with today's fabrication methods.

The amplifier in FIGS. 7A and 7B has a non-inverting and inverting input. The switches alternate whether the recorder is connected to one input or the other. Current trackers are applications of this idea.

In FIGS. 7A and 7B, $S_{E1}$ and $S_{E2}$ form the pair of electrodes used to record the signal. During operation, the two switches shown will always flip at the same time. Thus, in operation, after taking a measurement (say, A, at normal polarity, FIG. 7A), both switches are toggled before taking the next measurement (say, A', at inverted polarity, FIG. 7B). As discussed elsewhere herein, signals internal to the system will not invert and will therefore cancel out when taking the difference between signals recorded at the two different positions. Signals external to the system (such as from neurons) will invert and will sum and will therefore be reinforced. Changing the connections just inverts the signal, so performing the subtraction (A−A') is the same as calculating (A−(−A)), (which is identical mathematically to an addition). Dividing the sum of the two signals by two results in the neural response and stimulus artifact contributions alone, with any contribution that is independent of polarity having been cancelled out. (By contrast, summing the two signals, i.e., calculating A+A'(=A+(−A)), results in just the acquisition artifact and any residual noise.)

In one embodiment, every odd measurement is made at inverted polarity. By changing the connections to the amplifier (altering the switch positions), the signal changes polarity.

It is beneficial to be able to switch the electrodes live, i.e., they are dynamically switched, meaning that it is not necessary to switch off the machine, or to stop recording, or to manually swap the lead wires to the electrodes or to move the electrodes themselves in order to change the polarity. In many embodiments, there is some software processing that controls the switching, which can be readily implemented by those of skill in the art.

The method described herein is applicable to a biophysical implant, but it can also be integrated with any device that has dynamic switching, for which there is a latency from stimulation, and for which an electrically measured, acoustically evoked response is measured.

EXAMPLES

Example 1: Bench Testing

In one application of the method, some exemplary measurements are presented. These measurements can be obtained using a device to emulate the behavior of real tissue, generating a simulated neural response over a replicated tissue network in response to electrical stimulation; or through animal studies, as is typical in the art.

Figure 6A:
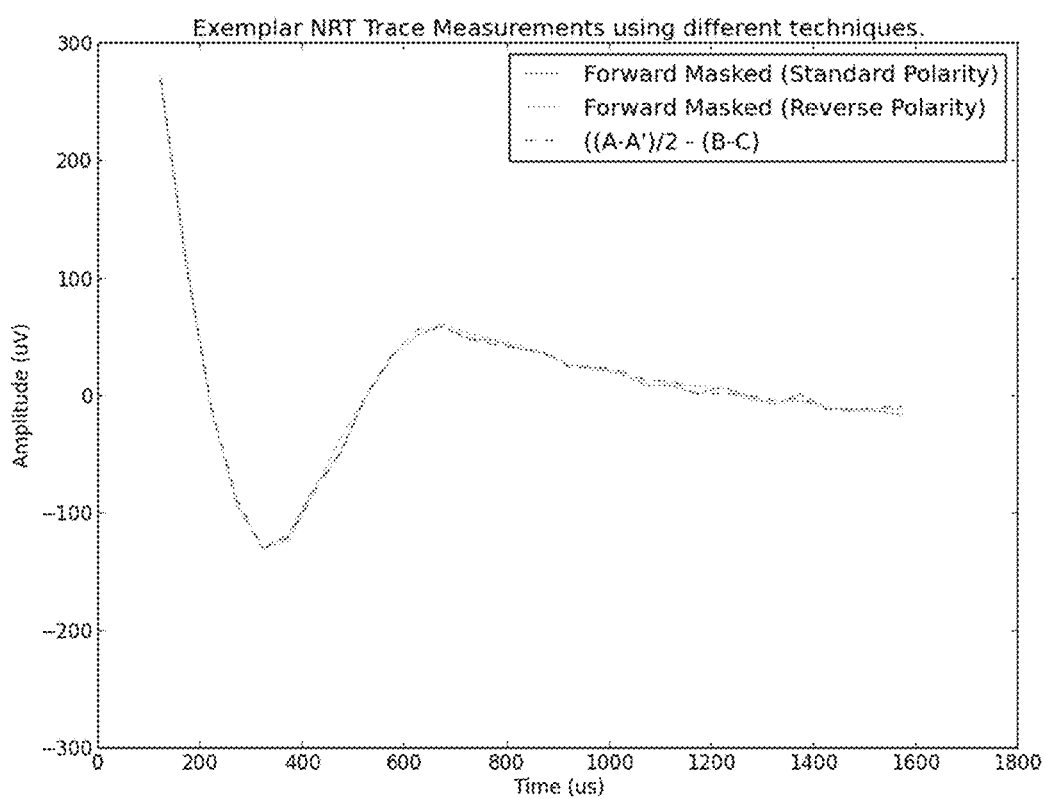
FIG. 6A shows a calculated neural response in an example measurement.
Figure 6B:
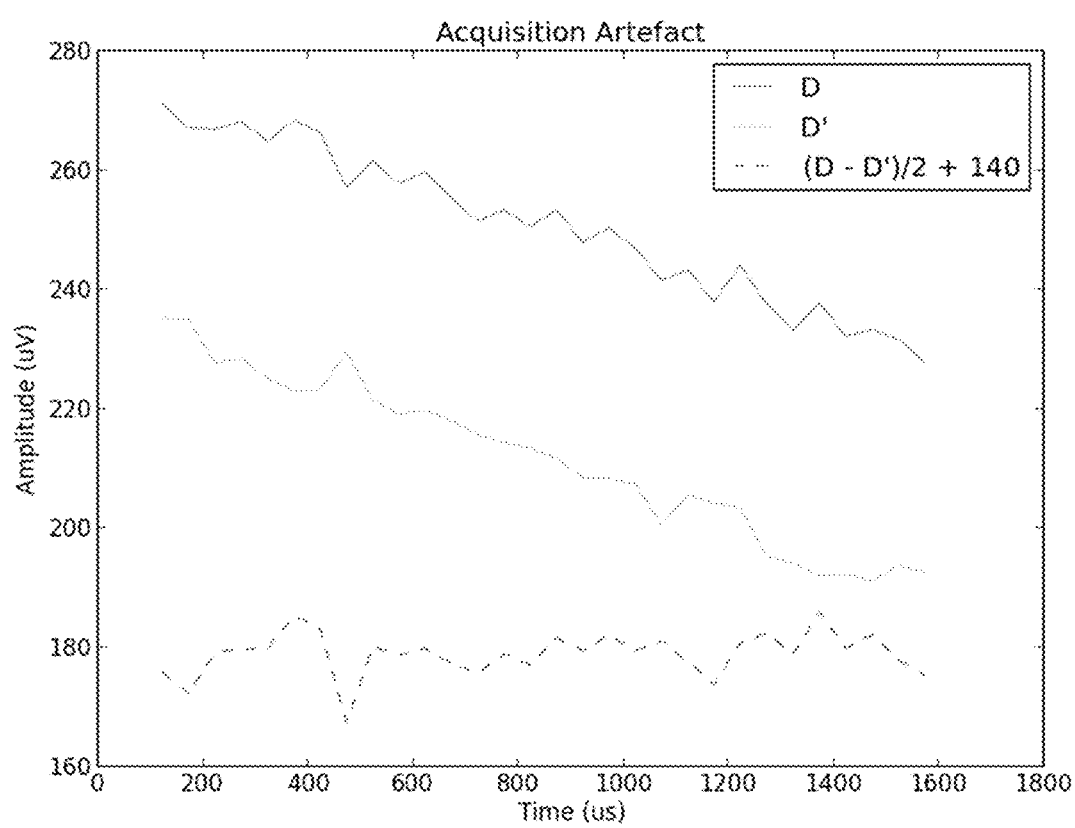
FIG. 6B shows acquisition (switch-on) artifact only for an example measurement.

For simplicity, the typical results from a standard, forward masked neural response telemetry (NRT) measurement are shown in FIG. 6A, and a typical amplifier artifact such as might be obtained from a typical measurement apparatus is shown in FIG. 6B. In FIGS. 6A and 6B, the "NRT Sample Number" on the abscissa is an analog for time, indicating the number of consecutive measurements, starting from the number 1, performed since acquisition began. The amplifier illustrated here provides a measurement approximately every 50 μs. The time of a specific measurement, with respect to stimulus onset, in this particular example can be calculated as [122 μs+(NRT Sample Number−1)*50 μs]. The overall form of the curves in FIG. 6A generally follows the expected stimulus/response curve for a neuron. The P0 component (first peak) of the neural response occurs before recording begins; the N1 component (first trough) is clearly visible (at sample number 6), as is the P1 component (the peak at sample number 17). The notation P0, P1, and N1, as applied to the curves, are a notation understood in the art.

Plotted in FIG. 6A is the neural response resulting from the standard forward masked NRT (dark gray, such as by the A-(B-(C-D)) technique as described elsewhere herein), and recording electrode inverted NRT (light gray). (The second trace has been shown inverted on the graph so that it is the same polarity as the standard forward masked trace, for ease of comparison.) It can be seen that the curves are very similar to one another across their range.

The NRT trace calculated according to the method described herein is also shown in FIG. 6A (dashed line). (The B and C traces referenced in the caption are the additional traces recorded to eliminate the stimulus artifact and are not shown separately in the figure.) The DC offsets were subtracted from all of the traces so that they align with one another.

The dark gray and light gray curves on the trace in FIG. 6A illustrate that swapping the polarity doesn't make much difference overall to the signal. The dashed line trace comes from the method herein.

That the acquisition artifact does not invert when the electrodes are inverted is shown in FIG. 6B, which displays epochs of the acquisition artifact as described elsewhere herein. Trace D (the baseline trace) is the switch on trace, which shows the acquisition artifact acquired in standard forward masked recording mode, while trace D' is the switch on trace acquired with the recording electrodes inverted. No stimulus was applied prior to the acquisition. Note that traces D and D' both have a linear downward trend with sample number. That trend is due to the acquisition artifact of this system. Note that reversing the polarity of the recording electrodes does not change the polarity of this artifact as predicted. There is an arbitrary DC offset of the two measurements with this system. The dashed line is the difference between these two switch on measurements, and displays as a flat line (aside from the residual noise).

The dark gray and light gray lines are the D-trace, (which is the baseline, measured in the absence of stimulation), with normal (D) and inverted (D') polarity, respectively. The dashed curve shows the result of calculating (D−D')/2, i.e., subtracting the light gray curve (D') from the dark gray (D) curve, which eliminates the acquisition artifact. The plotted curve has 140 μV added to the result of subtraction and averaging in order to display the curve on the same axes as D and D'. This is because there is some DC (mean) offset associated with the recordings in this exemplar. The amplifier has hardware to bring the signal into its dynamic range by compensating for the DC offset of the first sample. This introduces an arbitrary DC offset into the measurements and the final processed response, which has also been illustrated here with these offsets.

Note how, D & D' follow the same slow decreasing trend, illustrating the switch-on artifact for this implant. When these samples are averaged, the trace follows the decreasing trend found with the acquisition artifact, irrespective of recording polarity. It should be noted that, in general, an acquisition artifact is not necessarily revealed as a gradual or linear decay, and will depend on the characteristics of the measurement system being used.

By contrast, when the difference of the two acquisitions is taken (dashed line), the trace remains flat, demonstrating that the amplifier artifact has been canceled.

All references cited herein are incorporated by reference in their entireties.

The foregoing description is intended to illustrate various aspects of the instant technology. It is not intended that the examples presented herein limit the scope of the appended claims. The invention now being fully described, it will be apparent to one of ordinary skill in the art that many changes and modifications can be made thereto without departing from the spirit or scope of the appended claims.

What is claimed:

1. A method of measuring an in vivo electrical potential, the method comprising:
    applying at least a first electrical stimulus to at least one stimulating electrode of an implant;
    acquiring, via a set of recording electrodes, a first trace corresponding to one or more signals evoked in response to the at least first electrical stimulus during one or more first recording probe epochs during which the set of recording electrodes have a first polarity;
    changing a polarity of the set of recording electrodes from the first polarity to a second polarity, wherein the second polarity is inverted relative to the first polarity;
    applying at least a second electrical stimulus to the at least one stimulating electrode of the implant;
    acquiring, via the set of recording electrodes, a second trace corresponding to one or more signals evoked in response to the at least second electrical stimulus during one or more second recording epochs during which the set of recording electrodes have the second polarity; and
    determining a difference between the first and the second traces, thereby reducing an acquisition artifact.

2. The method of claim 1, wherein the in vivo electrical potential is a signal used in calibrating the implant.

3. The method of claim 1, wherein the in vivo electrical potential is an electrophysiological response.

4. The method of claim 3, wherein the electrophysiological response is an evoked compound action potential (ECAP).

5. The method of claim 3, wherein the electrophysiological response is an acoustic reflex threshold.

6. The method of claim 1, wherein at least one stimulating electrode is the same as at least one recording electrode in the set of recording electrodes.

7. The method of claim 1, wherein the implant comprises a differential amplifier, and the second polarity arises from inverting the polarity of the recording electrodes that are in electrical contact with the differential amplifier.

8. The method of claim 1, wherein the second polarity arises from dynamically switching the polarity.

9. The method of claim 8, wherein the switching occurs in a period of time between a pair of adjacent recording epochs.

10. The method of claim 1, wherein the determining a difference comprises subtracting a trace obtained during an epoch in which the set of recording electrodes have the first polarity from a trace obtained during a corresponding epoch in which the set of recording electrodes have the second polarity, and averaging the result.

11. The method of claim 1, wherein the implant is a cochlear implant.

12. The method of claim 1, wherein the implant is selected from: a brain implant, a spinal implant, and a retinal implant.

13. The method of claim 1, further comprising:
    acquiring a third trace corresponding to application of both an electrical stimulus and a secondary mask stimulus;
    acquiring a fourth trace corresponding to application of only a secondary mask stimulus; and
    subtracting the third and fourth traces from half of a result of subtracting the second trace from the first trace.

14. The method of claim 13, wherein the in vivo electrical potential is an ECAP.

15. The method of claim 13, wherein the implant is an auditory prosthesis.

16. The method of claim 13, wherein the implant is selected from: a brain implant, a spinal implant, and a retinal implant.

17. A system for measuring an evoked compound action potential (ECAP), the system comprising:
    an electrode array in electrical communication with a biological component, wherein the electrode array comprises a plurality of pairs of recording electrodes;
    a plurality of differential amplifiers, in electrical communication with the electrode array, whereby each electrode in a pair of recording electrodes is connected to an input of one of the differential amplifiers;
    a switching circuit in electrical communication with the differential amplifiers, and configured to invert a polarity of the inputs to one or more of the differential amplifiers; and
    instructions encoded in logical memory for:
        applying at least a first electrical stimulus via the electrode array, thereby generating an ECAP, wherein the ECAP comprises stimulus artifact, acquisition artifact, noise, and a target signal;
        recording, via a first pair of recording electrodes, a first trace corresponding to one or more signals evoked in response to the at least first electrical stimulus during one or more first recording probe epochs during which the first pair of recording electrodes have a first polarity;
        changing a polarity of the first pair of recording electrodes from the first polarity to a second polarity, wherein the second polarity is inverted relative to the first polarity;
        applying at least a second electrical stimulus via the electrode array;
        recording, via the first pair of recording electrodes, a second trace corresponding to one or more signals evoked in response to the at least second electrical stimulus during one or more second recording epochs during which the first pair of recording electrodes have the second polarity;

subtracting a trace obtained during an epoch in which the first pair of recording electrodes have the first polarity from a trace obtained during a corresponding epoch in which the first pair of recording electrodes have the second polarity, and averaging the result, thereby eliminating the acquisition artifact.

18. The system of claim 17, wherein the biological component is the cochlea of a subject.

19. The system of claim 17, wherein the electrode array is in an auditory prosthesis.

20. The system of claim 17, wherein the system is selected from: a brain implant, a spinal implant, and a retinal implant.

21. The system of claim 17, wherein none of the recorded epochs is a baseline trace.

* * * * *